(12) United States Patent
Destexhe et al.

(10) Patent No.: US 11,596,345 B2
(45) Date of Patent: Mar. 7, 2023

(54) PHYSIO-SENSORY TRANSDUCTION METHOD AND DEVICE

(71) Applicant: CENTRE NATIONAL DE LA RECHERCHE SCIENTIFIQUE, Paris (FR)

(72) Inventors: Alain Destexhe, Gif-sur-Yvette (FR); Luc Foubert, Gif-sur-Yvette (FR)

(73) Assignee: CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 653 days.

(21) Appl. No.: 16/607,704

(22) PCT Filed: Mar. 30, 2018

(86) PCT No.: PCT/EP2018/058290
§ 371 (c)(1),
(2) Date: Oct. 23, 2019

(87) PCT Pub. No.: WO2018/197155
PCT Pub. Date: Nov. 1, 2018

(65) Prior Publication Data
US 2020/0138322 A1 May 7, 2020

(30) Foreign Application Priority Data
Apr. 25, 2017 (FR) .................................. 1753609

(51) Int. Cl.
*A61B 5/00* (2006.01)
*A61B 5/372* (2021.01)
(Continued)

(52) U.S. Cl.
CPC .............. *A61B 5/369* (2021.01); *A61B 5/316* (2021.01)

(58) Field of Classification Search
None
See application file for complete search history.

(56) References Cited

U.S. PATENT DOCUMENTS

| 5,471,009 A | 11/1995 | Oba et al. |
| 2015/0201889 A1 | 7/2015 | Roginska et al. |
| 2018/0236232 A1* | 8/2018 | Soulet De Brugiere ................... A61N 1/36031 |

FOREIGN PATENT DOCUMENTS

| EP | 0301790 A2 | 1/1989 |
| WO | 9001897 A1 | 3/1990 |

(Continued)

OTHER PUBLICATIONS

Lovisa. Multi-sensory environments adaptation for the relaxation of children with neurodevelopmental disorders. 2016/2017. (Year: 2016).*

(Continued)

*Primary Examiner* — Etsub D Berhanu
(74) *Attorney, Agent, or Firm* — Greer, Burns & Crain, Ltd

(57) ABSTRACT

A method and device allowing a physiological signal, typically representative of brain activity, to be transcribed in the form of sensory signals perceptible to a human user, typically acoustic signals is provided. For this purpose, a physiological signal is acquired and then analysed in such a way as to detect therein patterns that are then parameterised in the time domain. One or more parameters of these patterns are used to determine one or more parameters of the generated sensory signals and/or to determine one or more parameters of temporal envelopes used to modulate the sensory signals. This method and device can be applied, in particular, to neuro-acoustic transduction.

17 Claims, 4 Drawing Sheets

(51) Int. Cl.
  *A61B 5/38*   (2021.01)
  *A61B 5/369*  (2021.01)
  *A61B 5/316*  (2021.01)

(56) References Cited

FOREIGN PATENT DOCUMENTS

WO       9749333 A1    12/1997
WO  WO-2017021662 A1 *  2/2017  ......... A61B 5/04001

OTHER PUBLICATIONS

Grand et al. Aesthetic strategies in sonification. AI & Soc (2012) 27:213-222. (Year: 2012).*
Hauksson. Automated Analysis of Newborn EEG. 2006. (Year: 2006).*
French Search Report from French Patent Application No. 1753609, dated Jan. 4, 2018.
International Search Report from corresponding International Patent Application No. PCT/EP2018/058290, dated Jul. 13, 2018.
Destexhe et al., "The Spikiss Project: Composing Music from Awake Neuronal Activity", Exploring Transdisciplinarity in Art and Sciences (2018), pp. 237-253.
Le Van Quyen et al., "High-Frequency Oscillations in Human and Monkey Neocortex During the Wake-Sleep Cycle", PNAS (2016), 113(33), pp. 9363-9368.

* cited by examiner

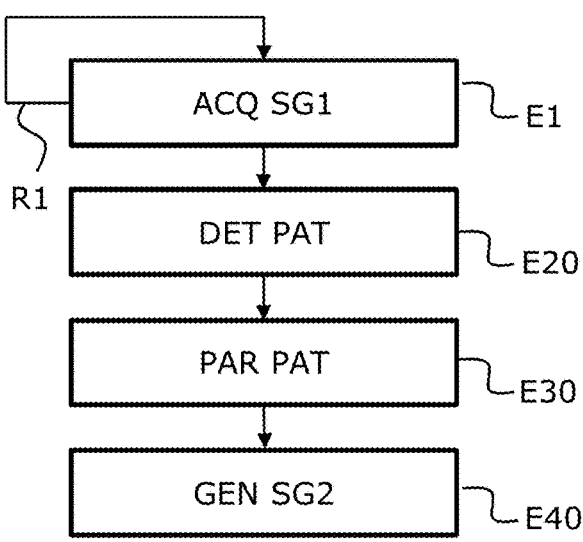
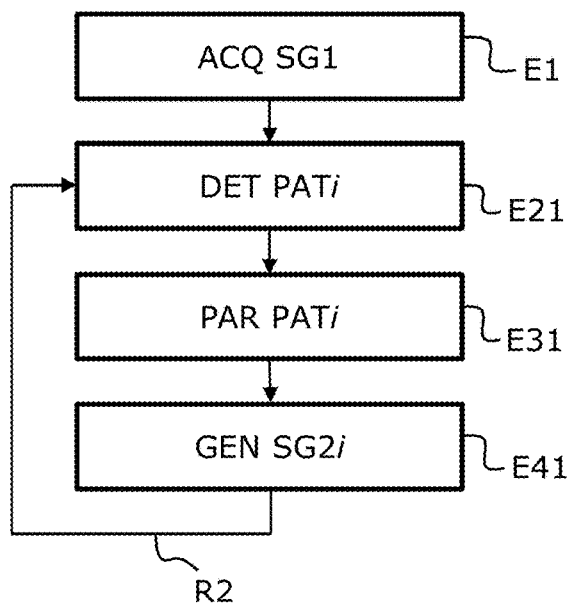
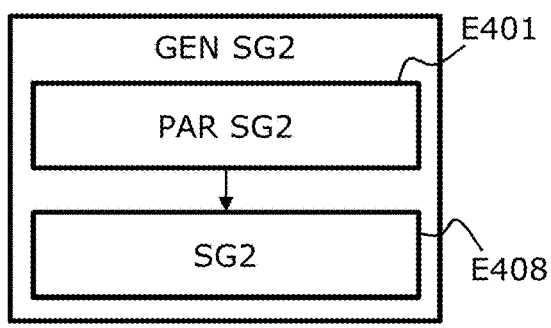
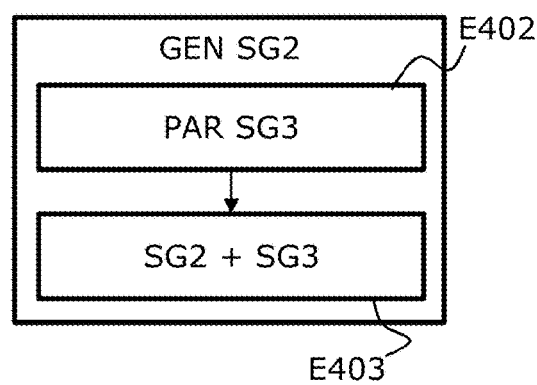
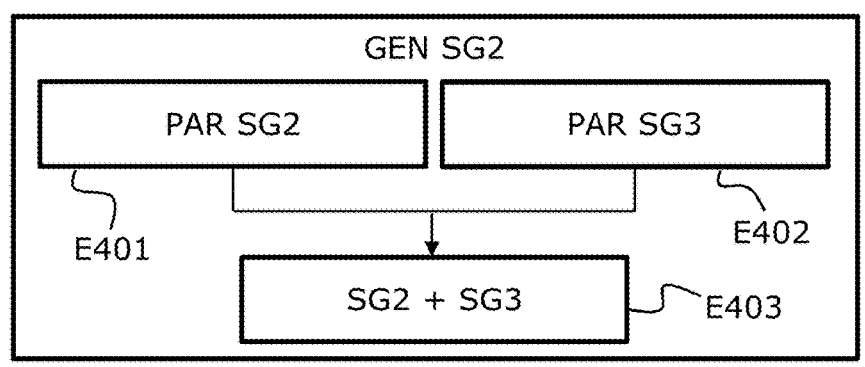

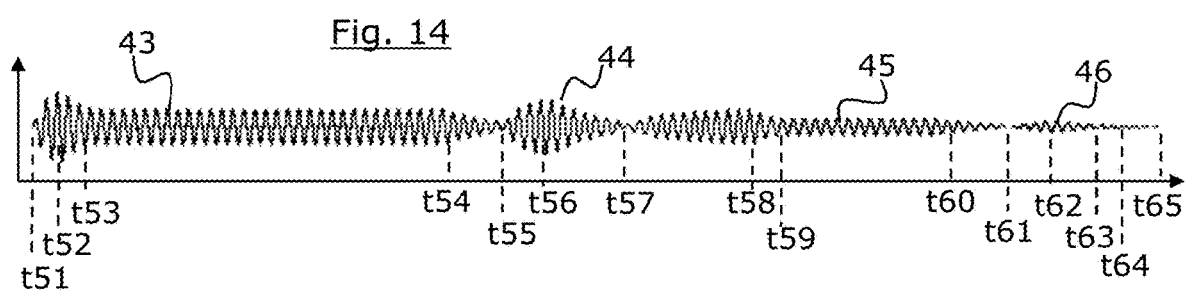

PHYSIO-SENSORY TRANSDUCTION METHOD AND DEVICE

BACKGROUND

The present invention relates to the fields of signal processing and sensory stimulation.

More specifically, the present invention relates to a method and a device for the transduction of a physiological signal into a sensory signal. Non-limitatively, the physiological signal can be representative of a brain activity of a human being and the sensory signal can be an acoustic signal.

Methods and devices intended to stimulate an individual's brain waves based on a brain activity measurement signal from this individual are known.

For example, in the patent application FR 3 039 773 A1, predefined patterns are identified in a physiological signal, in particular in order to identify slow brain waves representative of a state of sleep. These slow waves typically have a frequency comprised between 0.3 and 5 Hz. Based on these predefined patterns, an acoustic signal is emitted. The acoustic signal consists of a pink noise burst or of a signal of long duration before a slow wave period. In order to stimulate the brain waves, the acoustic signal is synchronized with a pattern identified in the physiological signal.

A purpose of the present invention is to improve, compared with the state of the prior art, the transcription of a physiological signal—in particular representative of a brain activity—in the form of a sensory signal—acoustic or other—perceptible to a human user.

SUMMARY

To this end, a first aspect of the invention relates to a physio-sensory transduction method comprising:
- an acquisition of a physiological signal from an organism (preferably a human being) and
- a detection of one or more patterns in the physiological signal, and also comprising, for each pattern detected:
- an extraction of at least one pattern parameter from the pattern detected, and
- a generation of a sensory signal associated with this pattern comprising:
  - a determination of at least one parameter of the sensory signal as a function of the at least one pattern parameter, and/or
  - a modulation of the sensory signal as a function of a temporal envelope associated with this pattern, having at least one envelope parameter determined as a function of the at least one pattern parameter.

Such a method makes it possible to improve, compared with the state of the prior art, the transcription of a physiological signal into a sensory signal, by the parameterization of the pattern(s) detected in the physiological signal and the generation of a sensory signal determined as a function of this parameterization.

As each detected pattern gives rise to its own sensory signal, a physiological signal comprising a succession of patterns will give rise to a respective succession of sensory signals.

Preferably, such a succession of sensory signals can be generated so as to respect the temporal arrangement of such a succession of patterns detected in the physiological signal. For example, three successive patterns detected in the physiological signal will preferably give rise to three sensory signals associated with these patterns and generated both in the same order and respecting time intervals between the patterns as detected in the physiological signal.

When several sensory signals, respectively associated with several successive patterns of a physiological signal, are generated successively, it is considered in the present application that the time at which each of these sensory signals is generated does not constitute a sensory signal parameter, i.e. does not constitute a parameter specific to a given sensory signal. In fact, the time at which each of these sensory signals is generated constitutes a parameter which governs the temporal arrangement of these sensory signals. For this reason, it is considered in the present application that the time at which each of these sensory signals is generated does not constitute an intrasensory signal parameter but constitutes an intersensory signal parameter. In other words, in the present application it is meant by default that a sensory signal parameter is an intrasensory signal parameter.

The physiological signal is preferably representative of a brain activity of the organism which can, for example, be measured by electroencephalography, or any other technique for recording brain activity.

Alternatively, the physiological signal is representative of a cardiac or respiratory or ocular or muscular activity of the organism.

The sensory signal is preferably an acoustic signal (acoustic wave having as signal parameter, for example, a duration and/or a frequency or frequencies and/or an intensity of this frequency or these frequencies) audible to a human being.

Alternatively, the sensory signal can be:
- a visual signal (image or light having as signal parameter, for example, a duration and/or an intensity or amplitude and/or a frequency or wavelength (of each pixel in the case of an image)) or
- tactile (mechanical pressure having as signal parameter, for example, a duration and/or a force and/or an amplitude of movement and/or a vibration frequency), or
- olfactory (odour having as signal parameter, for example, a duration and/or an intensity or amplitude and/or a scent), or
- gustatory (taste having as signal parameter, for example, a duration and/or an intensity or amplitude and/or a flavour).

In a preferred embodiment,
- the organism is a human being,
- the physiological signal is representative of a brain activity of said human being, and
- the sensory signal is an acoustic signal.

In an embodiment the pattern(s) detected in the physiological signal can be representative of a state of deep sleep. The pattern(s) detected can in this case consist of waves with a frequency comprised between 0.3 and 5 Hz called delta waves.

The detection of one or more patterns in the physiological signal can be carried out following any known procedure. For example, the detection of a pattern can comprise:
- detection of an amplitude of the physiological signal becoming greater than or equal to a first predetermined amplitude at a first time;
- detection of the amplitude of the physiological signal becoming less than a second predetermined amplitude at a second time;
- a validation test according to which a pattern is detected if the elapsed duration between said first and second times is greater than or equal to a predetermined duration.

Preferably, for each pattern detected, the at least one pattern parameter can result from a calculation or a measurement of:
- a pattern start time, and/or
- a pattern end time, and/or
- a maximum amplitude of the physiological signal in this pattern and/or
- a maximum amplitude time for which the sensory signal in this pattern reaches the maximum amplitude, and/or
- a total duration corresponding to an elapsed duration between said pattern start time and said pattern end time, and/or
- a duration of ascent corresponding to an elapsed duration between said pattern start time and said maximum amplitude time, and/or
- a duration of descent corresponding to an elapsed duration between said maximum amplitude time and said pattern end time, and/or
- a first and/or second derivative of the physiological signal between said pattern start time and said maximum amplitude time, and/or
- a first and/or second derivative of the physiological signal between said maximum amplitude time and said pattern end time.

For a given pattern, said pattern start time can preferably consist of said first time at which an amplitude of the physiological signal is detected becoming greater than or equal to said first predetermined amplitude.

In an embodiment, for each pattern detected, the generation of the sensory signal associated with this pattern can comprise said modulation of this sensory signal as a function of said temporal envelope associated with this pattern, the at least one envelope parameter being able to comprise:
- an attack amplitude corresponding to a maximum amplitude of the temporal envelope associated with this pattern, and/or
- an attack duration corresponding to an elapsed duration between a start time and a maximum amplitude time of the temporal envelope associated with this pattern, and/or
- a release duration corresponding to an elapsed duration between a release start time and an end time of the temporal envelope associated with this pattern, and/or
- a decay duration corresponding to an elapsed duration starting from the maximum amplitude time up to a decay end time, and/or
- a sustain amplitude, and/or
- a sustain duration corresponding to an elapsed duration between a decay end time and a release start time.

Thus, said temporal envelope can be an "ADSR"-type envelope (abbreviation for "Attack Decay Sustain Release"). Alternatively, the temporal envelope can be an "AR"- or "ASR"- or "ADR"-type envelope.

The release duration can also correspond to an elapsed duration starting from:
- the maximum amplitude time in the case of an AR-type envelope, or
- a sustain duration end time in the case of an ASR- or ADSR-type envelope, or
- a decay duration end time in the case of an ADR-type envelope.

The decay duration can also correspond to an elapsed duration up to:
- a release start time in the case of an ADR-type envelope, or
- a sustain start time in the case of an ADSR-type envelope.

In an embodiment, the at least one envelope parameter can comprise the attack amplitude, the attack duration and the extinction duration.

Preferably:
- the attack amplitude can depend on the maximum amplitude of the physiological signal in this pattern, and/or
- the attack duration can depend on the duration of ascent and/or
- the extinction duration can depend on the duration of descent.

In another embodiment, for each pattern detected:
- the generation of the sensory signal associated with this pattern can comprise said modulation of this sensory signal as a function of said temporal envelope associated with this pattern,
- the at least one pattern parameter can comprise a maximum amplitude of the physiological signal in this pattern,
- the at least one envelope parameter can comprise:
  - an attack amplitude being a function of said maximum amplitude of the physiological signal in this pattern and/or
  - an attack duration being a function of said maximum amplitude of the physiological signal in this pattern.

When the at least one envelope parameter comprises an attack amplitude, the attack amplitude can be proportional to the maximum amplitude.

When the at least one envelope parameter comprises an attack duration, the attack duration can be inversely proportional to the maximum amplitude.

In an embodiment, for each pattern detected, the generation of the sensory signal can comprise said determination of at least one sensory signal parameter, the at least one sensory signal parameter being able to comprise:
- an oscillation frequency, and/or
- a cutoff frequency, and/or
- an amplitude.

In an embodiment, for each pattern detected:
- the at least one pattern parameter can comprise a maximum amplitude of the physiological signal in this pattern,
- the sensory signal:
  - can be filtered with a filter having a cutoff frequency being a function of said maximum amplitude of the physiological signal in this pattern, the filter being for example a low-pass or high-pass filter, and/or
  - can oscillate with a frequency being a function of said maximum amplitude of the physiological signal in this pattern and/or
  - can have an amplitude being a function of said maximum amplitude of the physiological signal in this pattern.

In an embodiment, for each pattern detected, the at least one sensory signal parameter can vary as a function of a variation of the at least one pattern parameter, the at least one pattern parameter preferably being a maximum amplitude of the physiological signal in this pattern. According to this latter embodiment, the at least one sensory signal parameter can comprise an oscillation frequency, and/or a cutoff frequency, and/or an amplitude.

In general, several patterns can be detected in the physiological signal, each pattern being able to comprise as pattern parameter a pattern start time, each sensory signal generated for each pattern detected being able to comprise an initiation time of this sensory signal, the elapsed duration between the initiation time of each pair of sensory signals generated contiguously being able to be proportional or equal to the elapsed duration between the pattern start time of each pair of patterns detected contiguously.

In other words and consequently, the temporal dynamics of the sum of the sensory signals generated can match the temporal dynamics of the physiological signal.

In an embodiment, each pattern can also comprise as pattern parameter a pattern end time, each sensory signal generated for each pattern detected being able to also comprise an expiration time of this sensory signal, the amplitude of each sensory signal generated for each pattern detected being able to be constant between the initiation time and the expiration time of this sensory signal.

According to a first embodiment variant, the generation of said sensory signal is carried out in a deferred manner with respect to the acquisition of the physiological signal.

In other words, the generation of the sensory signal(s) can be preceded by a recording of computer data or of a digital or electronic or electric or analogue signal (for example a sound file) allowing the subsequent generation of the sensory signal(s).

According to a second embodiment variant, the detection of the pattern(s), the extraction of said at least one pattern parameter, and the generation of said sensory signal can be carried out in real time with respect to the acquisition of the physiological signal.

By the expression "real time" is meant that the processing of the physiological signal (or the different steps concerned) is carried out in such a way that the modulation of the sensory signal generated is representative of the physiological signal acquired at the same moment, plus or minus the time of implementation of the processing steps.

Thus, for example, when the sensory signal is modulated in such a way that the amplitude of this sensory signal is only non-zero between the pattern start time and the pattern end time for a given pattern, the sensory signal will have a non-zero amplitude synchronously with the presence of such a pattern in the physiological signal, with a time lag corresponding to the time of carrying out the steps of pattern detection, pattern parameter extraction, and sensory signal generation.

The sensory signal generated can be a periodic function (optionally modulated or not modulated by an envelope) or a non-periodic function.

In an embodiment, no step is implemented in order to transform the physiological signal from a time domain to a frequency domain.

A second aspect of the invention relates to a physio-sensory transduction device comprising:
  an acquisition means arranged and/or programmed in order to acquire a physiological signal from an organism, and
  a detection means arranged and/or programmed in order to detect one or more patterns in the physiological signal,
and also comprising:
  an extraction means arranged and/or programmed in order to extract at least one pattern parameter from each pattern detected, and
  a generation system arranged and/or programmed in order to generate a sensory signal for each pattern detected, this generation system comprising:
    a determination means arranged and/or programmed in order to determine at least one parameter of the sensory signal as a function of the at least one pattern parameter, and/or
    a modulation means arranged and/or programmed in order to modulate the sensory signal as a function of a temporal envelope associated with this pattern, having at least one envelope parameter determined as a function of the at least one pattern parameter.

Such a device makes it possible to implement the method described above.

In a preferred embodiment, the device can be arranged and/or programmed in such a way that:
  the organism can be a human being,
  the physiological signal is representative of a brain activity of said human being, and
  Ie sensory signal is an acoustic signal.

Preferably, the detection means can be arranged and/or programmed in order to:
  detect an amplitude of the physiological signal becoming greater than or equal to a first predetermined amplitude at a first time;
  detect the amplitude of the physiological signal becoming less than a second predetermined amplitude at a second time;
  carry out a validation test according to which a pattern is detected if the elapsed duration between said first and second times is greater than or equal to a predetermined duration.

Preferably, the detection means can comprise a calculator or a measurement tool arranged and/or programmed in order to carry out, for each pattern detected, a calculation or a measurement of:
  a pattern start time, and/or
  a pattern end time, and/or
  a maximum amplitude of the physiological signal in this pattern and/or
  a maximum amplitude time for which the sensory signal in this pattern reaches the maximum amplitude, and/or
  a total duration corresponding to an elapsed duration between said pattern start time and said pattern end time, and/or
  a duration of ascent corresponding to an elapsed duration between said pattern start time and said maximum amplitude time, and/or
  a duration of descent corresponding to an elapsed duration between said maximum amplitude time and said pattern end time, and/or
  a first and/or second derivative of the physiological signal between said pattern start time and said maximum amplitude time, and/or
  a first and/or second derivative of the physiological signal between said maximum amplitude time and said pattern end time,
and in order to assign the result of this calculation or of this measurement with respect to said at least one pattern parameter.

In an embodiment, the modulation means can be arranged and/or programmed so that the at least one envelope parameter comprises:
  an attack amplitude corresponding to a maximum amplitude of the temporal envelope associated with this pattern, and/or
  an attack duration corresponding to an elapsed duration between a start time and a maximum amplitude time of the temporal envelope associated with this pattern, and/or
  a release duration corresponding to an elapsed duration between a release start time and an end time of the temporal envelope associated with this pattern, and/or
  a decay duration corresponding to an elapsed duration starting from the maximum amplitude time up to a decay end time, and/or a sustain amplitude, and/or a sustain duration corresponding to an elapsed duration between a decay end time and a release start time.

In an embodiment, the modulation means can be arranged and/or programmed so that the at least one envelope parameter comprises the attack amplitude, the attack duration and the extinction duration.

Preferably:

the attack amplitude can depend on the maximum amplitude of the physiological signal in this pattern, and/or the attack duration can depend on the duration of ascent and/or the extinction duration can depend on the duration of descent.

In another embodiment, the device can comprise the modulation means, the device being able to be arranged and/or programmed in such a way that, for each pattern detected:

the at least one pattern parameter comprises a maximum amplitude of the physiological signal in this pattern, the at least one envelope parameter comprises:

an attack amplitude being a function of said maximum amplitude of the physiological signal in this pattern and/or an attack duration being a function of said maximum amplitude of the physiological signal in this pattern.

In an embodiment, the device can comprise the determination means, and be arranged and/or programmed in such a way that, for each pattern detected, the at least one sensory signal parameter comprises:

an oscillation frequency, and/or a cutoff frequency, and/or an amplitude.

In an embodiment, the device can be arranged and/or programmed in such a way that, for each pattern detected:

the at least one pattern parameter comprises a maximum amplitude of the physiological signal in this pattern, the sensory signal:

is filtered with a filter of the device, this filter having a cutoff frequency being a function of said maximum amplitude of the physiological signal in this pattern, the filter being for example a low-pass or high-pass filter, and/or oscillates with a frequency which is a function of said maximum amplitude of the physiological signal in this pattern and/or an amplitude which is a function of said maximum amplitude of the physiological signal in this pattern.

Thus, in an embodiment, the device can comprise a filter arranged and/or programmed in order to filter the sensory signal, the filter being able to have a cutoff frequency being a function of said maximum amplitude, the filter being for example a low-pass or high-pass filter.

In an embodiment, the device can be arranged and/or programmed in such a way that, for each pattern detected, the at least one sensory signal parameter varies as a function of a variation of the at least one pattern parameter, the at least one pattern parameter preferably being a maximum amplitude of the physiological signal in this pattern.

Preferably, the device can be arranged and/or programmed in order to detect several patterns in the physiological signal, each pattern being able to comprise as pattern parameter a pattern start time, each sensory signal generated for each pattern detected being able to comprise an initiation time of this sensory signal, the elapsed duration between the initiation time of each pair of sensory signals generated contiguously being able to be proportional or equal to the elapsed duration between the pattern start time of each pair of patterns detected contiguously.

In an embodiment, the device can be arranged and/or programmed in such a way that each pattern also comprises as pattern parameter a pattern end time, each sensory signal generated for each pattern detected being able to also comprise an expiration time of this sensory signal, the amplitude of each sensory signal generated for each pattern detected being able to be constant between the initiation time and the expiration time of this sensory signal.

According to a first embodiment variant, the generation system can also comprise a retarder arranged and/or programmed in order to generate the sensory signal in a deferred manner with respect to the acquisition of the physiological signal.

According to a second embodiment variant, the generation system can be a real-time generator arranged and/or programmed in order to detect the pattern(s), to extract said at least one pattern parameter, and generate said sensory signal in real time with respect to the acquisition of the physiological signal.

Preferably, the generation system can be arranged and/or programmed in such a way that the sensory signal generated is a periodic function.

In an embodiment, the device can be arranged and/or programmed so as not to implement any step in order to transform the physiological signal from a time domain to a frequency domain.

BRIEF DESCRIPTION OF THE DRAWINGS

Other advantages and features of the invention will become apparent on reading the detailed description of implementations and embodiments that are in no way limitative, and from the following attached drawings:

FIG. 4 is a diagram representing the main steps of the method according to the invention in a first implementation variant;

FIG. 5 is a diagram representing the main steps of the method according to the invention in a second implementation variant;

FIGS. 6 to 8 are diagrams representing different combinations of steps making it possible to generate a sensory signal according to the invention;

FIG. 14 shows a series of sensory signals generated according to a fourth mode of implementation of the invention;

DETAILED DESCRIPTION

In the different figures, the same references denote identical or similar characteristics or steps.

As the embodiments described hereinafter are in no way limitative, variants of the invention can be considered comprising only a selection of the characteristics described hereinafter, in isolation from the other characteristics described (even if this selection is isolated within a phrase containing other characteristics), if this selection of characteristics is sufficient to confer a technical advantage or to differentiate the invention with respect to the state of the art. This selection comprises at least one, preferably functional, characteristic without structural details, or with only a part of the structural details if this part alone is sufficient to confer a technical advantage or to differentiate the invention with respect to the state of the prior art.

The present invention typically aims to transcribe a physiological signal in the form of a sensory signal perceptible to a human user.

Physiological Signal

The physiological signal is preferably representative of a human brain activity.

The physiological signal is a temporal signal, i.e. a signal which is a function of a time.

The physiological signal has temporal dynamics, i.e. it varies over time.

Figure 1:
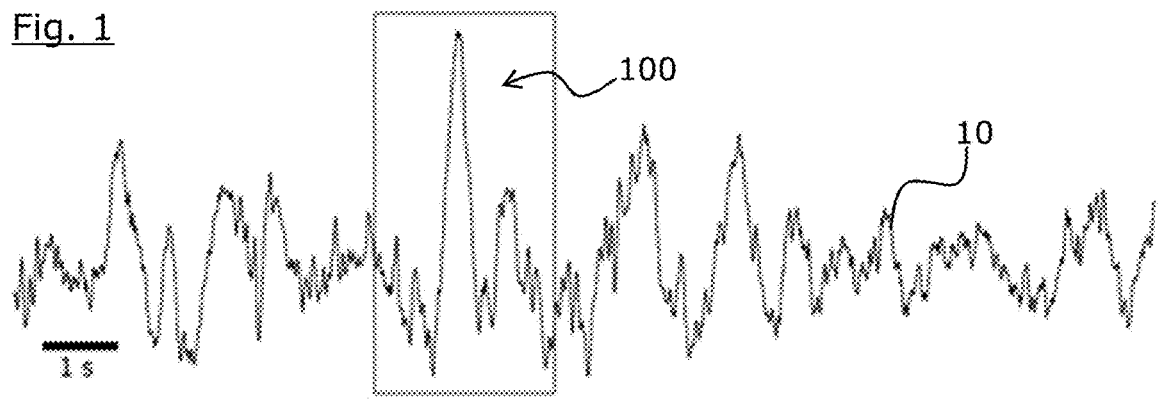
FIG. 1 shows a physiological signal recorded by electroencephalography on a human subject in deep sleep.

A first example of a physiological signal 10 is represented in FIG. 1. The signal 10 of FIG. 1 was obtained with the aid of an electroencephalogram recording the brain activity of a human being in a state of deep sleep.

Figure 9:
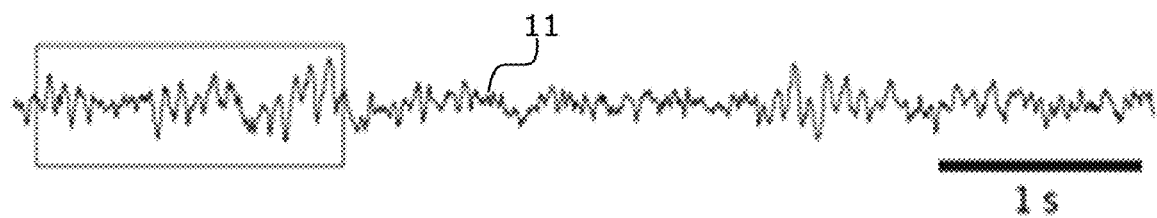
FIG. 9 shows a physiological signal recorded by electroencephalography on a wakeful human subject.

A second example of a physiological signal 11 is represented in FIG. 9. The signal 11 of FIG. 9 was obtained with the aid of an electroencephalogram recording the brain activity of a wakeful human being.

These different cognitive states of deep sleep or of wakefulness, are characterized by the presence of waves which oscillate at specific frequencies. Typically, in a state of deep sleep, the brain can generate waves, called delta waves, having a frequency comprised between 0.3 and 4 Hz. In a state of wakefulness, the brain can generate waves, called beta waves, typically having a frequency greater than 14 Hz.

The present invention is not limited to the acquisition or to the processing of the delta or beta waves and can be based on an acquisition of a physiological signal representative of a physiological activity, for example cerebral, cardiac, respiratory, ocular or else muscular—of any organism—for example an animal or a human being. This organism, in particular when the latter is an animal or a human being, can be placed in any cognitive state—for example in a state of deep or paradoxical sleep or of wakefulness or else of relaxation.

With reference to FIGS. 4 and 5, the method according to the invention is a physio-sensory transduction method comprising a step of acquisition E1 of a physiological signal, for example a physiological signal 10 or 11 as represented in FIG. 1 or 9. In the box E1 of the diagram of FIG. 4 and of FIG. 5, which corresponds to the step of acquisition of the physiological signal, "ACQ SG1" means "acquisition of the physiological signal".

Such an acquisition step E1 is carried out with the aid of a physio-sensory transduction device comprising an acquisition means arranged and/or programmed in order to acquire a physiological signal from an organism (not represented).

Pattern Detection

The method according to the invention comprises detection of one or more patterns in the physiological signal.

In the example of FIG. 4, the detection step E20 is carried out concurrently with the acquisition E1 of the physiological signal, which is illustrated by the loop R1 in the diagram of this FIG. 4. In the box E20 of the diagram of FIG. 4, which corresponds to the pattern detection step "DET PAT" means "pattern detection", it being understood that the pattern detected is a pattern present in a part of the physiological signal which has just been acquired.

In the example of FIG. 5, the detection step E21 is carried out after complete acquisition E1 of the physiological signal. In the box E21 of the diagram of FIG. 5, which corresponds to the pattern detection step "DET PATi" means "pattern detection", it being understood that the pattern detected is an i-th pattern present in the physiological signal acquired.

Alternatively or additionally, it is possible to detect one or more patterns in the physiological signal after partial acquisition of this signal.

Figure 2:
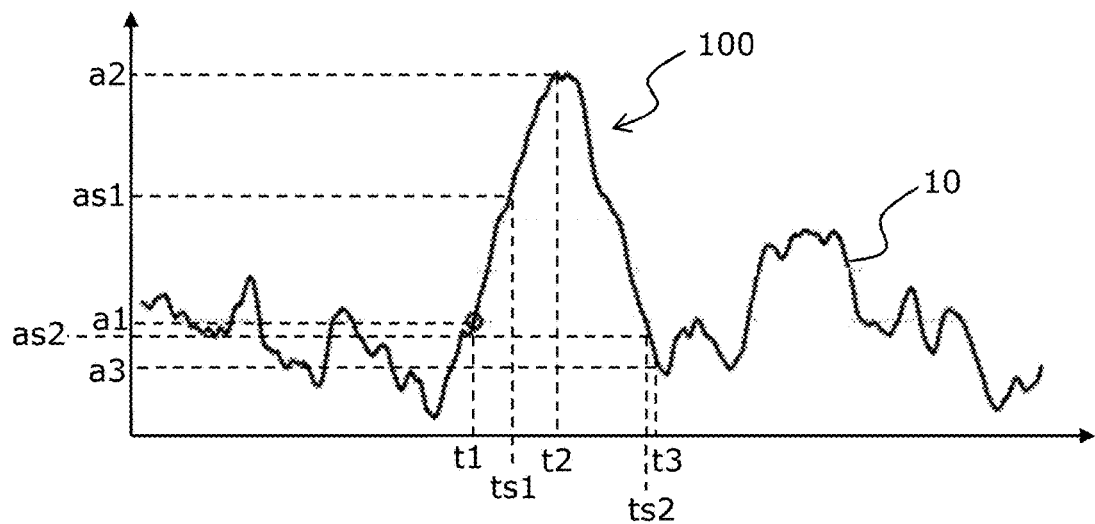
FIG. 2 shows a part of the physiological signal of FIG. 1.

FIG. 2 represents a part of the signal 10 of FIG. 1 (the part indicated by a rectangle in FIG. 1). FIG. 2 shows a pattern 100 which will be taken as an example in order to describe the invention hereinafter. In this example, the pattern 100 is representative of a state of deep sleep and corresponds to a delta wave.

Figure 10:
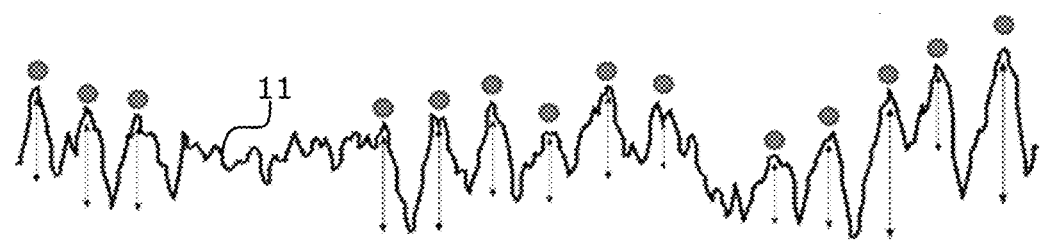
FIG. 10 shows a part of the physiological signal of FIG. 9.

FIG. 10 shows a part of the signal 11 of FIG. 9 (the part indicated by a rectangle in FIG. 9). In FIG. 10, several patterns of the signal 11 are denoted by solid circles situated above a maximum amplitude of each of these patterns. In this example, the patterns of FIG. 10 are representative of a state of wakefulness and correspond to beta waves.

In order to carry out the detection step E20 or E21, the physio-sensory transduction device comprises a detection means arranged and/or programmed in order to detect one or more patterns in the physiological signal (not represented).

In an embodiment, the detection E20 or E21 of a pattern 100 comprises the sub-steps SE1, SE2 and SE3 described below with reference to FIG. 2.

The sub-step SE1 comprises detection of the amplitude of the physiological signal 10 becoming greater than or equal to a first predetermined amplitude as1 at a first time ts1. For example, the first amplitude as1 can have a value of 7 µV.

FIG. 2 shows that said first time ts1 is typically situated after a pattern start time t1, which makes it possible to optimize the detection process by limiting the number of false detections.

The sub-step 5E2 comprises detection of the amplitude of the physiological signal 10 becoming less than a second predetermined amplitude as2 at a second time ts2. For example, the second amplitude as2 can have a value of 0.89 µV.

The value of the thresholds as1 and as2 can be proportional to a standard deviation of the physiological signal 10.

The sub-step SE3 comprises a validation test according to which a pattern 100 is detected if the elapsed duration between said first ts1 and second times ts2 is greater than or equal to a predetermined duration. For example, this predetermined duration can have a value of 100 ms. Such a test makes it possible in particular to avoid considering as a pattern any simple variation in the amplitude of the signal which may be linked to the high-frequency noise.

Parameterization

For each pattern 100 detected, the method comprises extraction of at least one pattern parameter from this pattern 100 detected.

In the example of FIG. 4, the extraction step E30 is carried out after the detection step for the pattern 100 detected during this latter detection step. In the box E30 of the diagram of FIG. 4, which corresponds to the step of extraction of at least one pattern parameter, "PAR PAT" means "pattern parameterization".

In the example of FIG. 5, the extraction step E31 is carried out after the step of detection of the i-th pattern 100 detected in the physiological signal. In the box E31 of the diagram of FIG. 5, which corresponds to the step of extraction of at least one pattern parameter, "PAR PATi" means "pattern parameterization", it being understood that the parameterized pattern is the i-th pattern detected in the physiological signal.

The extraction step is carried out by an extraction means comprised in the device of the invention, this extraction means being arranged and/or programmed in order to extract at least one pattern parameter from each pattern detected.

With reference to FIG. 2, for each pattern 100 detected, the at least one pattern parameter results from a calculation or a measurement of:
said pattern start time t1, and/or
a pattern end time t3, and/or
a maximum amplitude a2 of the physiological signal 10 in this pattern 100, and/or
a maximum amplitude time t2, and/or
a total duration corresponding to an elapsed duration between said pattern start time t1 and said pattern end time t3, and/or
a duration of ascent corresponding to an elapsed duration between said pattern start time t1 and said maximum amplitude time t2, and/or
a duration of descent corresponding to an elapsed duration between said maximum amplitude time t2, and said pattern end time t3, and/or
a first and/or second derivative of the physiological signal 10 between said pattern start time t1 and said maximum amplitude time t2, and/or
a first and/or second derivative of the physiological signal 10 between said maximum amplitude time t2 and said pattern end time t3.

In the present document, a first derivative is defined as a ratio of an amplitude variation to a time variation. For example, the first derivative of the physiological signal 10 between said pattern start time t1 and said maximum amplitude time t2 corresponds to the relationship between:
on the one hand, the difference in amplitude al of the physiological signal 10 at the time t1 and the maximum amplitude a2, and
on the other hand, the difference between t1 and t2.

Similarly, the first derivative of the physiological signal 10 between said maximum amplitude time t2 and said pattern end time t3 corresponds to the relationship between:
on the one hand, the difference between the maximum amplitude a2 and the amplitude a3 of the physiological signal 10 at the time t3, and
on the other hand, the difference between t2 and t3.

In the present document, a second derivative is defined as a variation of said first derivative with respect to said corresponding time variation.

By way of indicative example, the maximum amplitude a2 of the physiological signal 10 in the pattern 100 can be equal to 27 µV, the duration of ascent can be equal to 268 ms and the duration of descent can be equal to 348 ms.

In an embodiment (not shown), the detection means comprises a calculator or a measurement tool arranged and/or programmed in order to carry out, for each pattern detected, said calculation or said measurement and in order to assign the result of this calculation or of this measurement to said at least one pattern parameter.

Thus the method of the invention comprises, during the extraction step, a parameterization of the physiological signal 10 in the time domain.

Preferably, no step is implemented in order to transform the physiological signal 10 from a time domain to a frequency domain. In particular, the method according to the invention does not carry out any processing step in order to obtain a frequency representation of the physiological signal in order to extract the pattern parameter(s) therefrom. According to the invention, at least one and preferably all of the pattern parameters are extracts from the physiological signal in the time domain.

By means of this parameterization carried out in the time domain, the sensory signal can be generated so as to transcribe the physiological signal relatively faithfully from a perceptual point of view, in particular from the point of view of time perception.

Sensory Signal

According to the invention, a sensory signal is generated.

This sensory signal is preferably an acoustic signal or a wave but can alternatively or additionally be a signal or a wave of any other kind (visual, tactile, olfactory etc.) provided that it is perceptible to said organism.

The sensory signal is preferably a periodic function. For example, the sensory signal can consist of a sine wave or of a sum of sine waves.

For each pattern 100 detected, the method of the invention comprises generation of a sensory signal associated with this pattern 100 by means of a generation system arranged and/or programmed in order to generate such a signal.

In the example of FIG. 4, the step E40 of generation of a sensory signal is carried out after the extraction step E30. In the box E40 of the diagram of FIG. 4, which corresponds to this generation step, "GEN SG2" means "generation of a sensory signal".

In the example of FIG. 5, the step E41 of generation of a sensory signal is carried out after the extraction step E31. In the box E41 of the diagram of FIG. 5, which corresponds to this generation step, "GEN SG2i means "generation of a sensory signal", it being understood that the sensory signal generated is associated with the i-th pattern detected in the physiological signal during the step E21.

Irrespective of the embodiment, for example that illustrated in FIG. 4, the generation step E40 can comprise different sub-steps. Different combinations of sub-steps of step E40 are illustrated in FIGS. 6 to 8 with reference to the embodiment of FIG. 4. These different combinations can of course be applied to the embodiment of FIG. 5 or to any other embodiment according to the invention.

In the example of FIG. 6, the generation step E40 comprises a determination E401 of at least one parameter of the sensory signal as a function of the at least one pattern parameter extracted during the step E30.

In the box E401 of the diagram of FIG. 6, "PAR SG2" means "determination of at least one parameter of the sensory signal". When one or more sensory signal parameters are thus determined, the sensory signal is generated as such with the aid of the generation system (not represented), this effective generation being illustrated by the box E408 in the diagram of FIG. 6. In the box E408 of the diagram of FIG. 6, "SG2" means "effective generation of the sensory signal".

The at least one sensory signal parameter is, for example, an oscillation frequency, and/or a cutoff frequency, and/or an amplitude.

In order to carry out such a sub-step of determination of at least one parameter of the sensory signal, the generation system comprises a determination means arranged and/or programmed in order to determine at least one parameter of the sensory signal as a function of the at least one pattern parameter (not represented).

Another example is shown in FIG. 7 in which the generation step E40 comprises a modulation E403 of the sensory signal as a function of a temporal envelope associated with the pattern processed in the steps E20 and E30.

Such a temporal envelope consists of a specific signal constructed in order to modulate a sensory signal.

Figure 3:
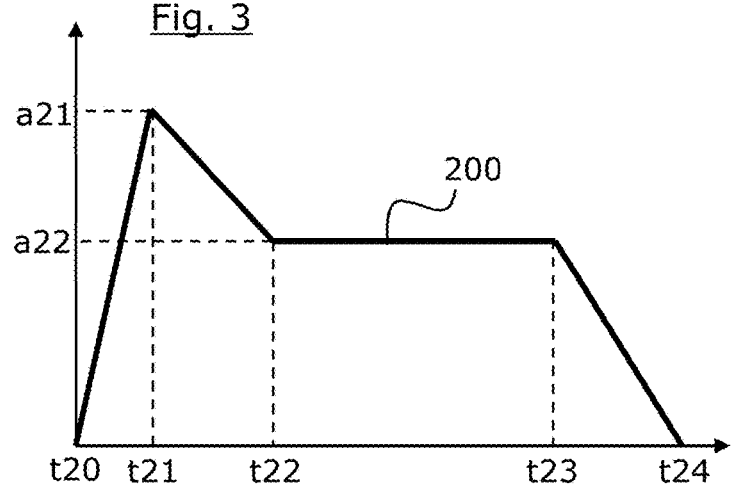
FIG. 3 shows an example of an "ADSR"-type envelope.

An example of a temporal envelope 200 is represented in FIG. 3.

According to the invention, for each pattern 100, a temporal envelope 200 can be associated with this pattern 100, and have at least one envelope parameter determined as a function of the at least one pattern parameter.

Thus, unlike the case of FIG. 6, in the case of FIG. 7:
the at least one pattern parameter is not assigned to one or more sensory signals parameters as such, but
the at least one pattern parameter determines at least one envelope parameter, which envelope serves to modulate the sensory signal.

In other words, in the example of FIG. 7, the generation step E40 comprises a sub-step of determination E402 of at least one envelope parameter. In the box E402 of the diagram of FIG. 7, "PAR SG3" means "determination of at least one envelope parameter". When one or more envelope parameters are thus determined, the sensory signal is modulated by the temporal envelope 200 and this thus-modulated sensory signal is then generated as such. This modulated sensory signal generation is illustrated by the box E403 in the diagram of FIG. 7. In the box E403 of this diagram "SG2+SG3" means "generation of the sensory signal modulated by the temporal envelope".

In order to carry out such a sub-step of modulation of the sensory signal, the generation system comprises a modulation means arranged and/or programmed in order to modulate the sensory signal as a function of a temporal envelope associated with the pattern that is the subject of the generation of this sensory signal, this temporal envelope having at least one envelope parameter determined as a function of the at least one pattern parameter.

The sensory signal generation according to the diagram of FIG. 8 combines the two approaches of FIGS. 6 and 7. In particular, the generation step E40 can thus comprise both:
a sub-step E401 of determination of at least one parameter of the sensory signal as a function of the at least one pattern parameter extracted during the step E30,
a sub-step E402 of determination of at least one envelope parameter as a function of the at least one pattern parameter extracted during the step E30, and
a sub-step E403 of generation of a modulated sensory signal.

In the box E403 of the diagram of FIG. 8, "SG2+SG3" means "generation of the sensory signal modulated by the temporal envelope", it being understood that the sensory signal is itself parameterized as a function of the at least one pattern parameter.

By way of non-limitative example, the generation system can comprise an amplifier, one or more oscillators, for example:
a monophonic oscillator capable of generating a wave of the sine, triangle-, square-wave type, etc.,
an oscillator of the "LFO" type (low-frequency oscillator),
a module making it possible to carry out additive or subtractive or frequency-modulation synthesis.
a wavetable reading module etc.

The device of the invention can implement analogue and/or digital technologies.

Temporal Envelope

A description will now be given of an example of a temporal envelope with reference to FIG. 3 which shows an ADSR-type envelope. Such an ADSR envelope comprises the following four successive phases: attack, decay (also called fall), sustain (also called holding) and release (also called extinction).

In the case of such an ADSR envelope associated with a given pattern 100, the at least one envelope parameter can comprise:
an attack amplitude a21 corresponding to a maximum amplitude of this temporal envelope 200, and for example proportional to the maximum amplitude of the associated pattern,
an attack duration corresponding to an elapsed duration between a start time t20 of this temporal envelope 200 and a maximum amplitude time t21, and for example proportional or equal to the duration of ascent of the associated pattern, or proportional to the maximum amplitude of the associated pattern,
a release duration corresponding to an elapsed duration from a sustain duration end time t23 up to an end time t24 of the temporal envelope 200, and for example proportional to the maximum amplitude or to the duration of descent of the associated pattern,
a decay duration corresponding to an elapsed duration starting from the maximum amplitude t21 up to a sustain start time t22, and for example proportional to the maximum amplitude or to the duration of descent of the associated pattern,
a sustain amplitude a22, and for example proportional to the maximum amplitude of the associated pattern,
a sustain duration corresponding to an elapsed duration between the decay end time t22 (which thus corresponds in this case to the sustain start time) and a release start time t23 (which thus corresponds in this case to the sustain duration end time), and for example proportional to the maximum amplitude or to the duration of descent of the associated pattern,
a total duration corresponding to an elapsed duration between the decay start time t20 and the decay end time t22, and for example proportional or equal to the total duration of the associated pattern, or proportional to the maximum amplitude of the associated pattern, By default:
the value of the amplitude a22 can be two-thirds of the amplitude a21, and/or
the decay duration and the release duration can each be equal to half the sustain duration.

The value of these envelope parameters can be defined by a value defined by default in the device according to the invention.

Other types of envelope, not represented, can be used, for example envelopes of the following types:
AR: comprising only attack and release phases;
ASR: comprising only attack, sustain and release phases;
ADR: comprising only attack, decay and release phases.

In the case of these other types of envelope, the different envelope parameters available are deduced from the list of parameters given below by way of example for an ADSR envelope.

Multiplicity of Sensory Signals

The preceding description essentially explains the generation of a sensory signal associated with a pattern detected in a physiological signal.

Of course, a physiological signal generally comprises several patterns which can each give rise to generation of its own sensory signal.

According to the variant of FIG. 4, the physiological signal is read concurrently with its acquisition (loop R1). As soon as a pattern is present in a part of the physiological signal being read, this pattern is in principle detected E20, triggering the carrying out of the steps E30 and E40. A sensory signal associated with this pattern is thus generated. Consequently, the presence of several patterns in different parts of the physiological signal is reflected by a successive generation of sensory signals associated with these different patterns.

The steps of detection E20 of the pattern(s), of extraction E30 of said at least one pattern parameter, and of generation E40 of said sensory signal can thus be carried out in real time with respect to the acquisition E1 of the physiological signal 10. In order to do this, the generation system can be a real-time generator arranged and/or programmed in order to detect the pattern(s), to extract said at least one pattern parameter, and generate said sensory signal in real time with respect to the acquisition of the physiological signal.

According to the variant of FIG. 5, the physiological signal is acquired in a prior or independent step E1. For each pattern i detected in the physiological signal during the step E21, the steps E31 and E41 are carried out. A sensory signal associated with each pattern i is thus generated. This pattern is processed separately, either in an iterative manner as illustrated by the loop R2, or in parallel (not represented). Consequently, the presence of several patterns in different parts of the physiological signal is reflected by a generation of sensory signals associated with these different patterns. When each pattern i is processed iteratively, the sensory signals associated with the patterns detected are successively generated in real time or optionally by passing through an intermediate recording in a memory of computer data or of a digital or electronic or electric or analogue signal (for example a sound file) allowing the subsequent generation of each sensory signal. When the patterns detected are processed in parallel, or when they are generated after recording of data in a memory, the sensory signals can be generated respecting or not respecting the temporality of the patterns in the physiological signal.

The generation of a sensory signal can thus be carried out in a deferred manner with respect to the acquisition of the physiological signal. In order to do this, the generation system can comprise a retarder arranged and/or programmed in order to generate the sensory signal in a deferred manner with respect to the acquisition of the physiological signal.

Preferably, several patterns 100 are detected in the physiological signal 10. In an embodiment, it is considered that each pattern 100 comprises as pattern parameter said pattern start time t1, and that each sensory signal generated for each pattern detected comprises an initiation time of this sensory signal. Preferably, according to this embodiment, the elapsed duration between the initiation time of each pair of sensory signals generated contiguously is proportional or equal to the elapsed duration between the pattern start time t1 of each pair of patterns detected contiguously.

Specific Examples

In an embodiment, the temporal envelope 200 comprises the following three envelope parameters: attack amplitude a21, the attack duration and the extinction duration. In this embodiment, for each envelope 200 associated with a given pattern 100:

the attack amplitude a21 depends on—for example is proportional to
the maximum amplitude a2 of the physiological signal 10 in this pattern 100, and/or
the attack duration depends on—for example is proportional to—the duration of ascent and/or
the extinction duration depends on—for example is proportional to—the duration of descent.

Figure 11:
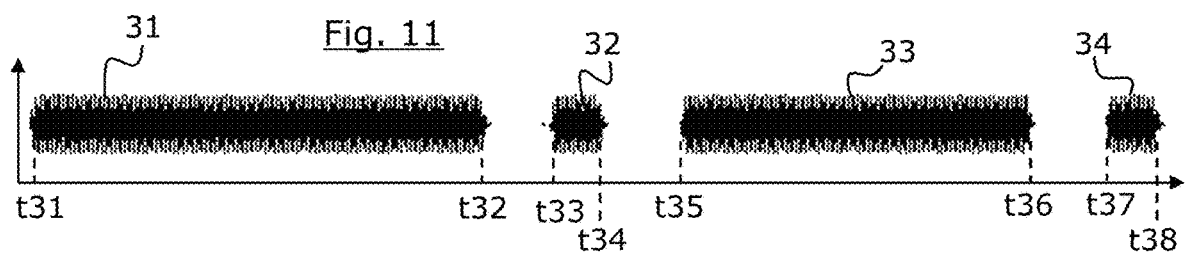
FIG. 11 shows a series of sensory signals generated according to a first mode of implementation of the invention.

In the embodiment MDR11 of FIG. 11, four sensory signals 31, 32, 33 and 34 are generated and correspond respectively to four patterns successively detected in a physiological signal, for example the signal 10 of FIG. 1. Each pattern 100 comprises as pattern parameter a pattern end time t3, and each sensory signal generated for each pattern detected comprises an expiration time of this sensory signal.

FIG. 11 shows that these four sensory signals 31, 32, 33 and 34 are respectively generated at an initiation time t31, t33, t35 and t37 and end respectively at an expiration time t32, t34, t36 and t38. It can also be seen that the amplitude, represented along the y-axis, of each sensory signal is constant between its initiation time and its expiration time.

The embodiment MDR11 thus illustrates a simple case in which each sensory signal has an identical amplitude irrespective of the shape of the pattern associated with this sensory signal—it is assumed hypothetically in this example that the patterns associated with the sensory signals 31, 32, 33 and 34 have a different shape, and have for example a different maximum amplitude.

FIG. 11 shows sensory signals 31, 32, 33 and 34 that differ in duration from one signal to another. It is assumed hypothetically in this example that each of the sensory signals 31, 32, 33 and 34 have a duration identical to the duration of the pattern associated therewith, the duration of a sensory signal being defined by the elapsed duration between its initiation time (for example t31 for the signal 31) and its expiration time (for example t32 for the signal 31).

For this embodiment MDR11 it is also assumed that, for illustration purposes, the elapsed duration between the initiation time of each pair of sensory signals generated contiguously is equal to the elapsed duration between the pattern start time of each pair of associated patterns detected contiguously in the physiological signal 10. In other words, the successive generation of the sensory signals 31, 32, 33 and 34 respects the temporal dynamics of the part of the physiological signal comprising the four patterns associated with these sensory signals.

Figure 12:
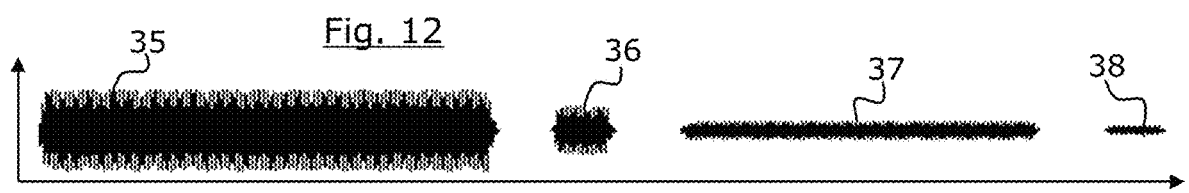
FIG. 12 shows a series of sensory signals generated according to a second mode of implementation of the invention.

The embodiment MDR12 of FIG. 12 is similar to the embodiment MDR11, with the exception of the respective amplitude of the sensory signals 35, 36, 37 and 38 which is a function of—for example proportional to—the maximum amplitude of the physiological signal in the corresponding pattern. It can thus be deduced from FIG. 12 that the maximum amplitude of the patterns associated with the sensory signals 35, 36, 37 and 38 is respectively smaller and smaller.

In other embodiments, the respective amplitude of the sensory signals 35, 36, 37 and 38 could be inversely proportional to the maximum amplitude of the physiological signal in the corresponding pattern, or be a function of any other kind, for example a function of this maximum amplitude and/or of one or more other pattern parameters.

Figure 13:
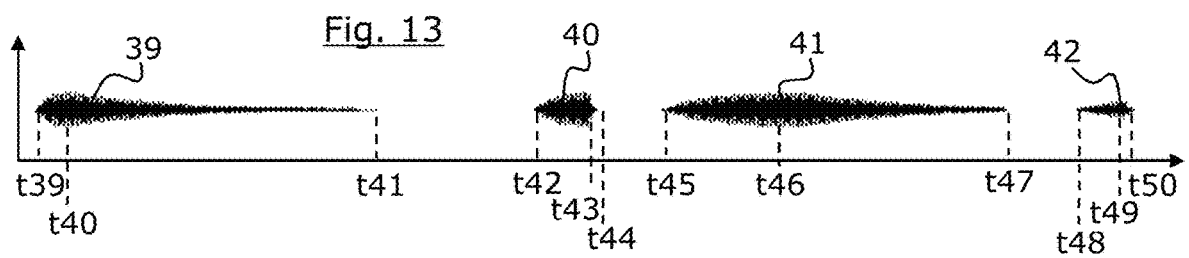
FIG. 13 shows a series of sensory signals generated according to a third mode of implementation of the invention.

FIG. 13 shows another embodiment MDR13 in which four sensory signals 39, 40, 41 and 42 are generated.

In this embodiment MDR13, for each pattern 100 detected in the physiological signal, the generation of the sensory signal associated with this pattern 100 comprises said modulation of this sensory signal as a function of said temporal envelope 200 associated with this pattern 100. As a consequence, it can be seen that the modulated sensory signals 39, 40, 41 and 42 each have a profile which evolves over time, in this instance have an amplitude which evolves over time due to the modulation of these signals by a temporal envelope, in this example an envelope of the AR type (see above for a description of different types of envelope). In this example, the at least one pattern parameter comprises a maximum amplitude a2 of the physiological signal 10 in this pattern 100, and the at least one envelope parameter comprises an attack duration a21 being proportional to said maximum amplitude a2 of the physiological signal 10 in the pattern associated with the corresponding envelope.

The sensory signals 39, 40, 41 and 42 are respectively generated at an initiation time t39, t42, t45 and t48 and end at an expiration time t41, t44, t47 and t50 respectively. These signals have a maximum amplitude time t40, t43, t46 and t49 respectively. The maximum amplitude reached by each of the sensory signals 39, 40, 41 and 42 is identical in absolute value from one signal to another but occurs after a duration of ascent that differs from one signal to another. The duration of ascent is defined by the elapsed duration between the initiation time (for example t39 for the signal 39) and the maximum amplitude time (for example t40 for the signal 39).

In another embodiment, not represented, the envelope parameter in the embodiment MDR13 is replaced by an envelope parameter comprising an attack amplitude a21 proportional to said maximum amplitude a2 of the physiological signal 10 in the pattern associated with the corresponding envelope.

The embodiment MDR14 of FIG. 14 combines the two latter embodiments which have just been described: the temporal envelope modulating each sensory signal has as envelope parameters both the attack duration and the attack amplitude. Furthermore, in the embodiment MDR14, the temporal envelope implemented is of the ADSR type.

More specifically, the sensory signals 43, 44, 45 and 46 of FIG. 14 have respectively:
an initiation time t51, t55, t57 and t61,
an expiration time t55, t57, t61 and t65 (in this example, the expiration time of the signals 43, 44 and 45 correspond to the initiation time of the signals 44, 45 and 46 respectively),
a maximum amplitude time t52, t56, t58 and t62,
a decay end time t53, t57 (for the signal 44, the decay end time corresponds to the expiration time of this signal), t59 and t63,
a release start time t54, t56 (for the signal 44, the release start time corresponds to the maximum amplitude time of this signal), t60 and t64.

The example of FIG. 14 shows that successively generated sensory signals can reach a maximum amplitude that differs from one signal to another, this maximum amplitude being able to occur after a duration of ascent that differs from one signal to another, by means of a parameterization as described above.

In the embodiment MDR15, for each pattern 100 detected, the at least one pattern parameter comprises a maximum amplitude a2 of the physiological signal 10 in this pattern 100, and the sensory signal is filtered with a filter having a cutoff frequency being a function of said maximum amplitude a2 of the physiological signal 10 in this pattern 100.

In other embodiments, not represented, which can be combined in particular with the embodiment MDR15, for each pattern 100 detected, the at least one pattern parameter comprises a maximum amplitude a2 of the physiological signal 10 in this pattern 100, and the sensory signal can:
oscillate with a frequency being a function of said maximum amplitude a2 of the physiological signal 10 in this pattern 100 and/or
have an amplitude being a function of said maximum amplitude a2 of the physiological signal 10 in this pattern 100.

In another embodiment, not represented, for each pattern 100 detected, the at least one sensory signal parameter varies as a function of a variation of the at least one pattern parameter, the at least one pattern parameter preferably being a maximum amplitude a2 of the physiological signal 10 in this pattern 100. The at least one sensory signal parameter can comprise an oscillation frequency and/or a cutoff frequency and/or an amplitude.

Of course, the invention is not limited to the examples which have just been described and numerous adjustments may be made to these examples without exceeding the scope of the invention For example, the method can comprise a step of detection of all of the patterns contained in a physiological signal followed by a classification step making it possible to select detected patterns representative of a particular cognitive state. Such a classification step can be useful, in particular in a situation in which the chosen pattern detection criteria are capable of detecting patterns representative of different cognitive states between which it is desired to make a distinction. This could be the case after acquisition of a physiological signal representing a brain activity over a prolonged duration, such as one night.

Furthermore, the different characteristics, forms, variants and embodiments of the invention can be combined together in various combinations, to the extent that they are not incompatible or mutually exclusive.

The physiological signal can be representative of a brain activity of the organism (alpha, beta, delta waves etc.) or of a cardiac or respiratory or ocular or muscular activity of the organism of an animal or human being. The physiological signal is not acquired from this animal or human being in an invasive manner, for example not by means of an intracerebral probe.

As explained above, the sensory signal can be an acoustic or visual or tactile or olfactory or gustatory signal. The sensory signal is preferably received (for example heard) by the same animal or human being from which or from whom the physiological signal has originated. The term "personalized" sensory signal is then used.

This sensory signal can be replayed in a personalized manner to the same individual who produced the sensory signal, or more generally to another user.

Of course, the different characteristics, forms, variants and embodiments of the invention can be combined together in various combinations.

The invention claimed is:

1. A physio-sensory transduction method comprising:
   an acquisition of a physiological signal of an organism using acquisition means; and
   a detection of one or more patterns in the physiological signal using detection means; for each pattern detected:
      an extraction of at least one pattern parameter from the pattern detected using extraction means; and
      a generation of a sensory signal associated with this pattern comprising:
         a determination of at least one parameter of the sensory signal as a function of the at least one pattern parameter using determination means; and
         a modulation of the sensory signal as a function of a temporal envelope associated with this pattern using modulation means, the temporal envelope having at least one envelope parameter determined as a function of the at least one pattern parameter.

2. The method according to claim 1, in which the detection of the one or more patterns comprises:
   a detection of an amplitude of the physiological signal becoming greater than or equal to a first predetermined amplitude at a first time;
   a detection of the amplitude of the physiological signal becoming less than a second predetermined amplitude at a second time ts2; and
   a validation test according to which a pattern is detected if the elapsed duration between said first and second times is greater than or equal to a predetermined duration.

3. The method according to claim 1 in which, for each pattern detected, the at least one pattern parameter results from a detection, a calculation or a measurement of:
   a pattern start time; and/or
   a pattern end time; and/or
   a maximum amplitude of the physiological signal in this pattern; and/or
   a maximum amplitude time; and/or
   a total duration corresponding to an elapsed duration between said pattern start time and said pattern end time; and/or
   a duration of ascent corresponding to an elapsed duration between said pattern start time and said maximum amplitude time; and/or
   a duration of descent corresponding to an elapsed duration between said maximum amplitude time, and said pattern end time; and/or
   a first and/or second derivative of the physiological signal between said pattern start time and said maximum amplitude time; and/or
   a first and/or second derivative of the physiological signal between said maximum amplitude time and said pattern end time.

4. The method according to claim 1, in which for each pattern detected, the at least one envelope parameter comprising:
   an attack amplitude corresponding to a maximum amplitude of the temporal envelope associated with this pattern; and/or
   an attack duration corresponding to an elapsed duration between a start time and a maximum amplitude time of the temporal envelope associated with this pattern; and/or
   a release duration corresponding to an elapsed duration starting from a release start time up to an end time of the temporal envelope associated with this pattern; and/or
   a decay duration corresponding to an elapsed duration starting from the maximum amplitude time up to a decay end time; and/or
   a sustain amplitude; and/or
   a sustain duration corresponding to an elapsed duration between the decay end time and a release start time.

5. The method according to claim 4, in which the at least one envelope parameter comprises the attack amplitude, the attack duration and an extinction duration, and in which:
   the attack amplitude depends on the maximum amplitude of the physiological signal in this pattern; and/or
   the attack duration depends on a duration of ascent; and/or
   the extinction duration depends on a duration of descent.

6. The method according to claim 4, in which for each pattern detected:
   the at least one pattern parameter comprises a maximum amplitude of the physiological signal in this pattern;
   the at least one envelope parameter comprises:
      the attack amplitude being a function of said maximum amplitude of the physiological signal in this pattern; and/or
      the attack duration being a function of said maximum amplitude of the physiological signal in this pattern.

7. The method according to claim 1, in which for each pattern detected, the at least one parameter of the sensory signal comprising:
   an oscillation frequency; and/or
   a cutoff frequency; and/or
   an amplitude.

8. The method according to claim 1, in which for each pattern detected:
   the at least one pattern parameter comprises a maximum amplitude of the physiological signal in this pattern, and
   the sensory signal:
      is filtered with a filter having a cutoff frequency being a function of said maximum amplitude of the physiological signal in this pattern; and/or
      oscillates with a frequency being a function of said maximum amplitude of the physiological signal in this pattern; and/or
      has an amplitude being a function of said maximum amplitude of the physiological signal in this pattern.

9. The method according to claim 1, in which for each pattern detected, the at least one parameter of the sensory signal varies as a function of a variation of the at least one pattern parameter, the at least one pattern parameter being a maximum amplitude of the physiological signal in this pattern.

10. The method according to claim 1, in which several patterns are detected in the physiological signal, each pattern comprising as a one of the at least one pattern parameter pattern start time, each sensory signal generated for each pattern detected comprising an initiation time of this sensory signal, the elapsed duration between the initiation time of each pair of consecutive sensory signals generated contiguously being proportional or equal to the elapsed duration between the pattern start time of each pair of consecutive patterns detected contiguously.

11. The method according to claim 10, in which each pattern also comprises as one of the at least one pattern parameter a pattern end time, each sensory signal generated for each pattern detected also comprising an expiration time of this sensory signal, the amplitude of each sensory signal generated for each pattern detected being constant between the initiation time and the expiration time of this sensory signal.

12. The method according to claim 1, in which the generation of said sensory signal is carried out in a deferred manner with respect to the acquisition of the physiological signal.

13. The method according to claim 1, in which the detection of the one or more patterns, the extraction of said at least one pattern parameter, and the generation of said sensory signal are carried out in real time with respect to the acquisition of the physiological signal.

14. The method according to claim 1, in which the sensory signal generated is a periodic function.

15. The method according to claim 1, in which no step is implemented in order to transform the physiological signal from a time domain to a frequency domain.

16. The method according to claim 1, in which:
the organism is a human being;
the physiological signal is representative of a brain activity of said human being; and
the sensory signal is an acoustic signal.

17. A physio-sensory transduction device comprising:
an acquisition means arranged and/or programmed in order to acquire a physiological signal from an organism; and
a detection means arranged and/or programmed in order to detect one or more patterns in the physiological signal;
an extraction means arranged and/or programmed in order to extract at least one pattern parameter from each pattern detected; and
a generation system arranged and/or programmed in order to generate a sensory signal for each pattern detected, this generation system comprising:
 a determination means arranged and/or programmed in order to determine at least one parameter of the sensory signal as a function of the at least one pattern parameter; and
 a modulation means arranged and/or programmed in order to modulate the sensory signal as a function of a temporal envelope associated with this pattern, having at least one envelope parameter determined as a function of the at least one pattern parameter.

* * * * *